US00PP13935P29

(12) United States Plant Patent
Hendriks

(10) Patent No.: US PP13,935 P2
(45) Date of Patent: Jul. 8, 2003

(54) CHLOROPHYTUM PLANT NAMED 'BONNIE'

(75) Inventor: Adri Hendriks, Voorschoten (NL)

(73) Assignee: New Variety, Elburg (NL)

( * ) Notice: Subject to any disclaimer, the term of this patent is extended or adjusted under 35 U.S.C. 154(b) by 0 days.

(21) Appl. No.: 10/210,621

(22) Filed: Jul. 31, 2002

(51) Int. Cl.[7] ..... A01H 5/00

(52) U.S. Cl. ..... Plt./373

(58) Field of Search ..... Plt./373

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Chlorophytum plant named 'Bonnie', characterized by its rounded and compact plant habit; dark green and white bi-colored foliage; and curled, reflexed and twisted leaves.

1 Drawing Sheet

BOTANICAL CLASSIFICATION/CULTIVAR DESIGNATION

*Chlorophytum comosum* cultivar Bonnie.

BACKGROUND OF THE INVENTION

The present Invention relates to a new and distinct cultivar of Chlorophytum plant, botanically known as *Chlorophytum comosum,* and hereinafter referred to by the cultivar name Bonnie.

The new Chlorophytum is a naturally-occurring whole plant mutation of *Chlorophytum comosum* 'Variegatum', not patented. The new Chlorophytum was discovered and selected by the Inventor as a plant within a population of plants of the parent selection in a controlled environment in Voorschoten, The Netherlands in 1998.

Asexual reproduction of the new cultivar by cuttings taken at Voorschoten, The Netherlands in June, 1999, has shown that the unique features of this new Chlorophytum are stable and reproduced true to type in successive generations.

SUMMARY OF THE INVENTION

The following traits have been repeatedly observed and are determined to be the unique characteristics of 'Bonnie'. These characteristics in combination distinguish 'Bonnie' as a new and distinct Chlorophytum cultivar:

1. Rounded and compact plant habit.
2. Dark green and white bi-colored foliage.
3. Curled, reflexed and twisted leaves.

Plants of the new Chlorophytum differ from plants of the parent cultivar and other known cultivars of Chlorophytum primarily in leaf orientation as plants of the parent selection and other known cultivars have flat leaves that do not curl, reflex or twist.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Chlorophytum. The photograph comprises a side perspective view of a typical plant of 'Bonnie' grown in a container.

DETAILED BOTANICAL DESCRIPTION

The cultivar Bonnie has not been observed under all possible environmental conditions. The phenotype may vary somewhat with variations in environment such as temperature and light intensity, without, however, any variance in genotype. The aforementioned photograph and the following observations and measurements describe plants grown in Voorschoten, The Netherlands under commercial practice in a glass-covered greenhouse with day and night temperatures about 19 to 22° C. Plants used in the photograph and following description were about one year old and grown in 11-cm containers. In the following description, color references are made to The Royal Horticultural Society Colour Chart, 1995 Edition, except where general terms of ordinary dictionary significance are used.

Botanical classification: *Chlorophytum comosum variegatum* cultivar Bonnie.

Parentage: Naturally-occurring whole plant mutation of *Chlorophytum comosum* 'Variegatum', not patented.

Propagation:

*Type.*—By cuttings.

*Time to initiate roots.*—About 18 days at 20° C.

*Time to produce a rooted cutting or liner.*—About 86 to 126 days at 19 to 22° C.

*Root description.*—Fibrous and freely branching.

Plant description:

*General appearance.*—Basal rosette of leaves. Rounded and compact; upright and outwardly spreading plant form. Appropriate for 11-cm containers.

*Growth and branching habit.*—Leaves developing at the base, dense and bushy growth.

*Plant height.*—About 16 cm.

*Plant diameter.*—About 35 cm.

*Foliage description.*—Arrangement: Rosette; simple. Length: About 31 cm. Width: About 2.5 to 3 cm. Shape: Linear. Apex: Sharply acute to acuminate. Base: Sessile. Margin: Entire. Texture, upper and lower surfaces: Smooth, glabrous. Aspect: Curled, reflexed and twisted. Color: Upper surface: At margins, between 137A to 147A; center, close to 155A. Lower surface: At margins, between 137B; center, close to 155A. Venation, upper and lower surfaces: Same as lamina.

Flower description:

*Flower type and flowering habit.*—Single rotate flowers arranged on basal panicles; about four flowers per panicle. Flowers persistent. Flowers not fragrant.

*Flowering season.*—Year-round under greenhouse conditions.

*Flower diameter.*—About 2 cm.

*Flower depth.*—About 1 cm.

*Flower buds.*—Length: About 1 cm. Diameter: About 2 cm. Shape: Ovoid. Color: Close to 144A.

*Perianth.*—Arrangement: Six segments per flower; separate. Segment length: About 8 mm. Segment width: About 3 mm. Margin: Entire. Texture: Smooth; glabrous. Color, upper and lower surfaces: Close to 155B.

*Peduncles.*—Length: About 18 cm. Diameter: About 1 cm. Texture: Smooth, glabrous. Color: Close to 144A.

*Pedicels.*—Length: About 1 cm. Diameter: About 1 mm. Texture: Smooth, glabrous. Color: Close to 144A.

Reproductive organs:

*Androecium.*—Quantity of stamens: Six per flower. Stamen length: About 1 cm. Anther shape: Oblong. Anther color: Close to 155A. Amount of pollen: Scarce to moderate. Pollen color: Close to 155D.

*Gynoecium.*—Pistil length: About 1 cm. Stigma color: Close to 155A. Style color: Close to 155A. Ovary color: Close to 144C.

Seed/fruit: Seed and fruit development has not been observed.

Disease/pest resistance: Plants of the new Chlorophytum have not been observed to be resistant to pathogens and pests common to Chlorophytum.

Temperature tolerance: Plants of the new Chlorophytum have been observed to tolerate temperatures from 10 to 30° C.

It is claimed:

1. A new and distinct cultivar of Chlorophytum plant named 'Bonnie', as illustrated and described.

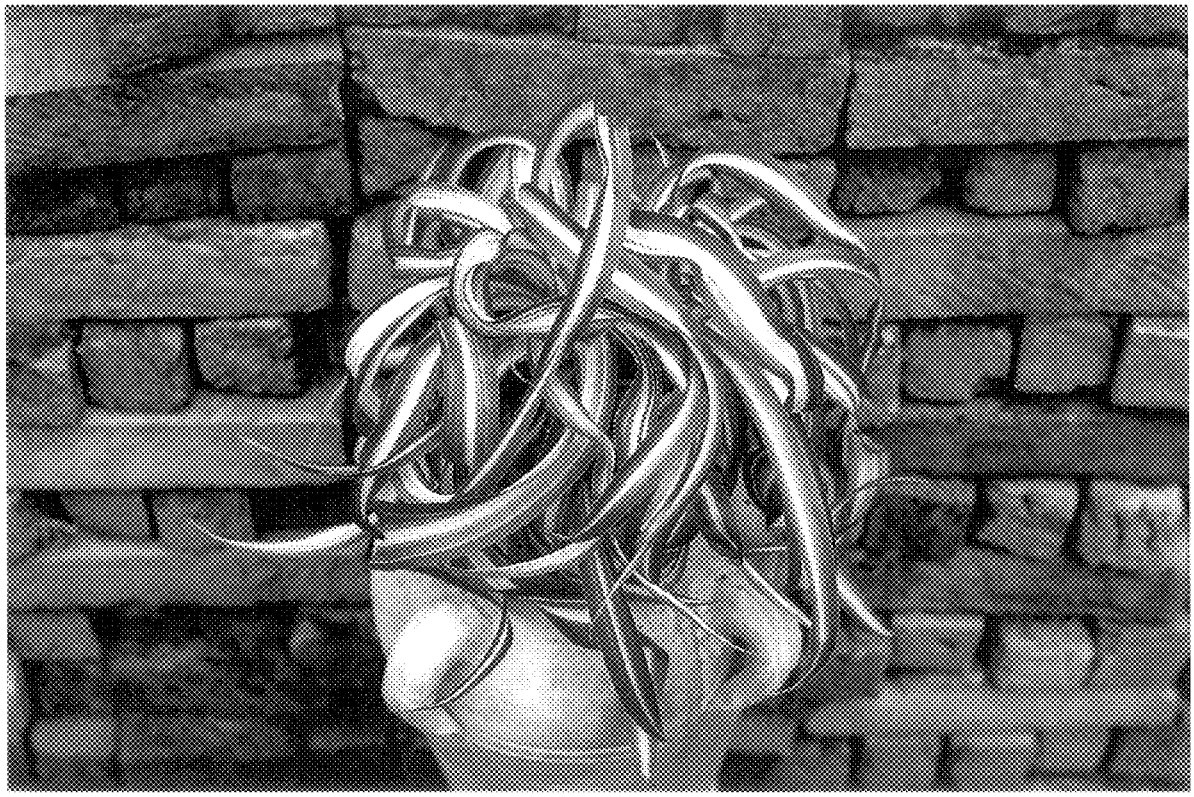

* * * * *